United States Patent
Beach et al.

(10) Patent No.: US 11,425,939 B2
(45) Date of Patent: Aug. 30, 2022

(54) GARMENT

(71) Applicant: Splash About International Limited, Lincolnshire (GB)

(72) Inventors: Lesley Ann Beach, Lincolnshire (GB); Brigit Elizabeth Maria Cheeseman, Lincolnshire (GB); Bernadette Spofforth, Lincolnshire (GB)

(73) Assignee: SPLASH ABOUT INTERNATIONAL LIMITED, Grimsby (GB)

( * ) Notice: Subject to any disclaimer, the term of this patent is extended or adjusted under 35 U.S.C. 154(b) by 0 days.

(21) Appl. No.: 16/347,430

(22) PCT Filed: Nov. 2, 2017

(86) PCT No.: PCT/GB2017/053299
§ 371 (c)(1),
(2) Date: May 3, 2019

(87) PCT Pub. No.: WO2018/083474
PCT Pub. Date: May 11, 2018

(65) Prior Publication Data
US 2019/0328047 A1    Oct. 31, 2019

(30) Foreign Application Priority Data

Nov. 3, 2016  (GB) ..................................... 1618569

(51) Int. Cl.
*A41B 13/04*  (2006.01)
*A41D 7/00*  (2006.01)
(Continued)

(52) U.S. Cl.
CPC .............. *A41B 13/04* (2013.01); *A41D 7/005* (2013.01); *A61F 13/494* (2013.01); *A61F 13/496* (2013.01)

(58) Field of Classification Search
CPC ........... A41B 13/04; A41B 9/04; A41B 9/001; A41B 9/12; A41B 9/14; A41B 13/045;
(Continued)

(56) References Cited

U.S. PATENT DOCUMENTS 2,256,510 A * 9/1941 Young ............... A61F 13/49003
604/386
2,466,545 A * 4/1949 Hessel ................... A41B 13/04
2/407

(Continued)

FOREIGN PATENT DOCUMENTS

EP    1205171 A2    5/2002
GB     674725 A  *  7/1952 ............. A41B 9/007
(Continued)

OTHER PUBLICATIONS

International Search Report and Written Opinion for PCT/GB2017/053299 dated Feb. 2, 2018; 8 pages.

*Primary Examiner* — Amy Vanatta
(74) *Attorney, Agent, or Firm* — Schwabe, Williamson & Wyatt, PC

(57) ABSTRACT

A garment, in particular a swim nappy, with an improved fit and formed from one or more substantially impermeable panels (6, 7, 8, 9) intended, in use, to cover a wearer's body between the waist and thighs. A top edge of the rear of the garment extends beyond the top edge of the front of garment in use so that the garment extends further up the wearer's back than the wearer's front. The top edge of the back of the garment may be convex, and the top edge of the front of the garment may be concave. The top edge of the garment may be formed by a waist band.

14 Claims, 6 Drawing Sheets

(51) Int. Cl.
*A61F 13/496* (2006.01)
*A61F 13/494* (2006.01)

(58) Field of Classification Search
CPC .......... A41D 7/005; A41D 11/00; A41D 1/06; A41D 1/089; A41D 31/10; A61F 13/494; A61F 13/496; A61F 2013/15195; A61F 13/15; A41F 9/00; A41F 9/02
See application file for complete search history.

(56) References Cited

U.S. PATENT DOCUMENTS

| | | | |
|---|---|---|---|
| 2,560,192 A | | 7/1951 | Seidner |
| 2,638,900 A | * | 5/1953 | Gruenberg ............. A41B 13/04 |
| | | | 2/408 |
| 2,739,314 A | * | 3/1956 | Friedman ................ A41B 9/02 |
| | | | 2/403 |
| 3,512,179 A | * | 5/1970 | Stamatiou ............. A41D 7/005 |
| | | | 2/67 |
| 4,669,130 A | * | 6/1987 | Brown .................... A41D 1/06 |
| | | | 2/227 |
| 6,080,038 A | * | 6/2000 | Sano ....................... A41C 1/003 |
| | | | 128/100.1 |
| 2002/0183706 A1 | | 12/2002 | Valentin |
| 2008/0039813 A1 | | 2/2008 | Ford |
| 2009/0077720 A1 | * | 3/2009 | Shinomiya ............. A41B 9/001 |
| | | | 2/401 |
| 2013/0072888 A1 | * | 3/2013 | Zorin ...................... A61F 13/72 |
| | | | 604/372 |
| 2013/0219589 A1 | * | 8/2013 | Jones ....................... A41D 1/06 |
| | | | 2/227 |
| 2013/0316617 A1 | * | 11/2013 | Freddi .................... A41D 31/18 |
| | | | 450/95 |
| 2014/0026293 A1 | * | 1/2014 | Quistian, Jr. ............ A41D 1/06 |
| | | | 2/227 |
| 2016/0353811 A1 | * | 12/2016 | Wallace ................. A41D 1/084 |

FOREIGN PATENT DOCUMENTS

| | | | | |
|---|---|---|---|---|
| GB | 2507084 A | | 4/2014 | |
| JP | S646105 A | | 1/1989 | |
| JP | 4734479 B1 | * | 7/2011 | ............ A41B 9/001 |
| WO | 2007/001381 A2 | | 1/2007 | |

* cited by examiner

GARMENT

CROSS-REFERENCE TO RELATED APPLICATION

The present application is a national phase entry under 35 U.S.C. § 371 of International Application No. PCT/GB2017/053299, filed Nov. 2, 2017, which designates the United States of America, which claims priority to GB Application No. 1618569.6, filed Nov. 3, 2016, the entire disclosures of each of these applications are hereby incorporated by reference in their entireties and for all purposes.

TECHNICAL FIELD OF THE INVENTION

The present invention relates to a garment and particularly, but not exclusively, to swimwear, a swim nappy or diaper.

BACKGROUND TO THE INVENTION

Swim nappies are worn by babies and very young children whilst in water, such as when learning to swim. They are intended to minimise the risk of faecal leaks and therefore contamination of the water, in particular swimming pools In practice, current swim nappies are not 100% effective in retaining faecal matter as it is difficult to obtain a good seal between the nappy and a wearer whilst producing a garment that is safe and comfortable to wear. Consequently, faecal matter can and does find its way into swimming pool water. This is undesirable.

Embodiments of the present invention seek to address this problem and it is an object of these embodiments to reduce (or eliminate) leakage of faecal matter discharged by a wearer into swimming pool water.

SUMMARY OF THE INVENTION

According to a first aspect of the present invention there is provided a garment formed from substantially impermeable panels and intended, in use, to cover a wearer's body between the waist and thighs, the garment comprising: a waist band formed from one or more panels of material, the waist band having a top edge and bottom edge, the top edge being shorter than the bottom edge and the bottom edge being joined to a top edge of the remainder of the garment, and two rear panels joined together along adjacent curved edges, the garment being shaped so that, in use, the top edge of the waist band at the rear of the garment extends beyond the top edge of the waist band at the front of the garment so that the garment extends further up the wearer's back than the wearer's front.

Increasing the height of the back of the garment relative to the front enables the front of the garment to sit below a natural point of bend to the wearer, and the back to sit above the wearer's coccyx thus lying above the natural concavity in the lower back. This both reduces the risk of the front of the garment rolling down and the back of the garment coming out of contact with the wearer and thus reduces the risk of material contained in the garment escaping.

Providing a waist band with a top edge shorter than a bottom edge, and constructing a rear of the garment from two panels joined together along adjacent curved edges, contributes to a better fit, especially over the wearer's waist. This also reduces the risk of material contained in the garment escaping.

The top edge of the back of the garment may be convex. The top edge of the front of the garment may be concave. The top edge of the garment may form a smooth curve around its periphery.

The waist band may have a substantially constant depth. The waist band may be formed from two or more panels of material, for example a fabric. One or more panels of material forming the waist band may be substantially trapezoidal in shape and the shorter parallel side or sides of the panels may form the top edge of the waist band.

The waist band may be formed from a resiliently stretchable fabric. The fabric may be of a type known as a high stretch fabric. It may be a knitted, such as tricot knit, fabric or a woven fabric. It may include a proportion of elastic fibre such as a natural or synthetic rubber, e.g. elastane (spandex). It may comprise at least 20% or at least 25% elastic fibre. The remainder may be a natural or synthetic fibre, such as nylon.

The top edge of the front of the remainder of the garment may be concave and/or the top edge of the rear of the remainder of the garment may be convex. That is to say, the shape of the ultimate top edge of the garment is created by the shape of the top edge of the remainder of the garment and not the waist band.

Alternatively it is possible for the waist band to be shaped to create and/or contribute to the desired shape of the top edge of the garment. As such the waist band may comprise a rear portion having a convex top edge and/or a front portion comprising a concave top edge.

The two rear panels may be mirror opposites and may be joined together along adjacent opposed curved edges. The opposed curved edges may have both concave and convex portions. Shaping the rear panels in this way enables the garment to better fit to the contours of a wearer's buttocks.

The garment may comprise a front panel having opposite side edges each joined to a respective side edge of a rear panel.

The garment may comprise a crotch panel intended to extend between a wearer's legs in use.

The front, rear and crotch panels may themselves be formed by a single panel or two or more panels joined together to produce a panel of desired overall shape. The panels may be formed from a resiliently stretchable material. The panels may be formed from a sheet material laminated with a fabric on one or both sides. The panels may be formed from a material with a higher elastic modulus than material forming waist and/or leg bands.

The crotch panel may be joined to a lower edge of each rear panel, and a lower edge of any front panel.

Panels of the garment may be joined together by any suitable means. Stitching is suitable. Panels may be joined with their adjacent edges abutting, such as by using flat lock stitching. Or panels may be joined by a seam, ideally positioned to the inside of the garment. Other joining techniques could of course be used such as using an adhesive or welding.

The waist band may extend above the top edge of the garment by a distance which is at least 10%, 15%, 20%, 25% or 30% of the shortest distance between a point on a lower edge of the front or rear panel to which the crotch panel is joined and a top edge of the front or rear panel at which the waist band is joined. The greater the depth (or width) of the waist band the more effectively it can help contain material within the garment, in use. For example, for a garment intended to be worn by a baby or infant under the age of 3 years the waist band preferably has a depth of at least 5, 6, 7 or 8 cm.

The garment may comprise leg bands which may be resiliently stretchable and may be formed from the same material as the waist band as discussed above.

A seal may be disposed around the inside of each leg opening and or waist opening arranged to form a seal with a wearer's body, in use. The seal may be formed by a strip of sealing material, such as a strip of natural or synthetic rubber or silicone rubber.

The garment may have the form of a brief or a pair of shorts or trunks or a swimsuit. The garment may be a swim nappy.

According to another aspect of the invention there is provided a method of reducing contamination of a swimming pool by an individual comprising the steps of:

providing a garment according to the first aspect of the invention with or without any of its discussed optional features; and wearing of the garment, by the individual, whilst in the swimming pool.

DETAILED DESCRIPTION OF THE INVENTION

In order that the invention may be more clearly understood embodiments thereof will now be described, by way of example only, with reference to the accompanying drawings, of which:

In what follows the terms top, bottom, side, inside, outside, front and rear are used to describe the garments in the orientation shown in the figures, which is the orientation they would adopt when worn by a person standing upright, and should not be taken to be otherwise limiting.

Figure 1:
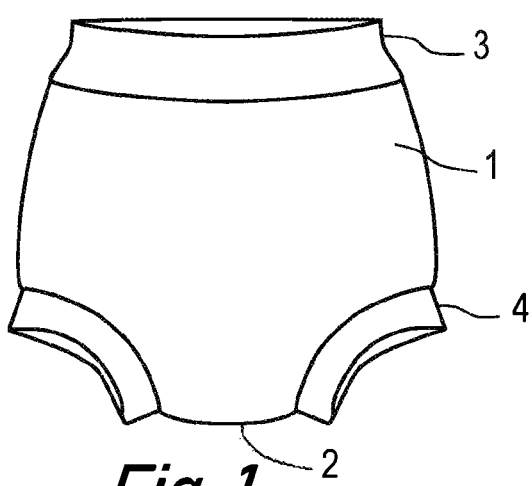
FIG. 1 is a front view of a conventional swim nappy.
Figure 2:
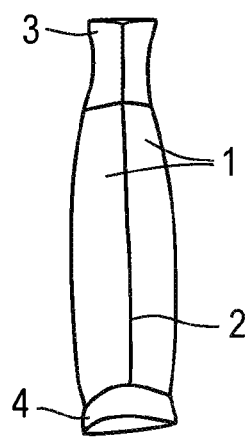
FIG. 2 is a side view of the nappy of FIG. 1.
Figure 3:
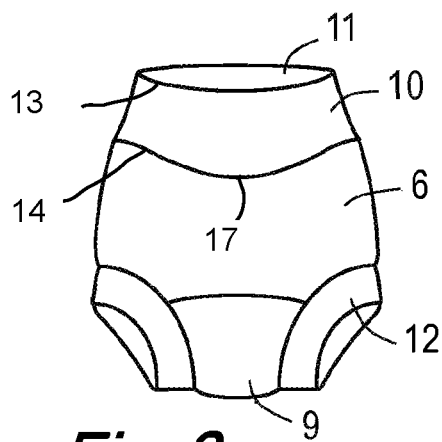
FIG. 3 is a front view of an embodiment of a swim nappy according to the invention.
Figure 4:
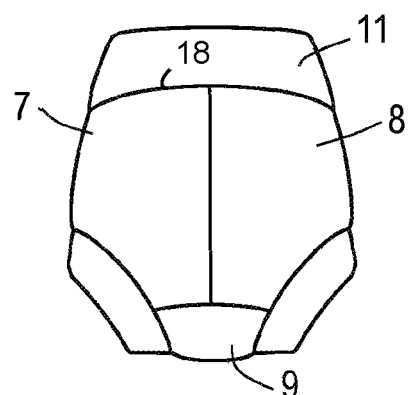
FIG. 4 is a rear view of the swim nappy of FIG. 3.
Figure 5:
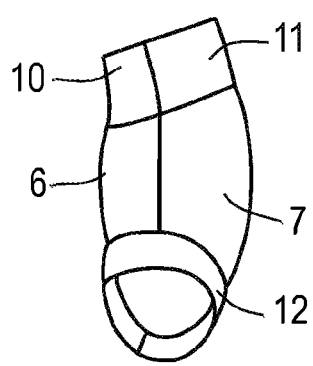
FIG. 5 is a side view of the swim nappy of FIG. 3.
Figure 6:
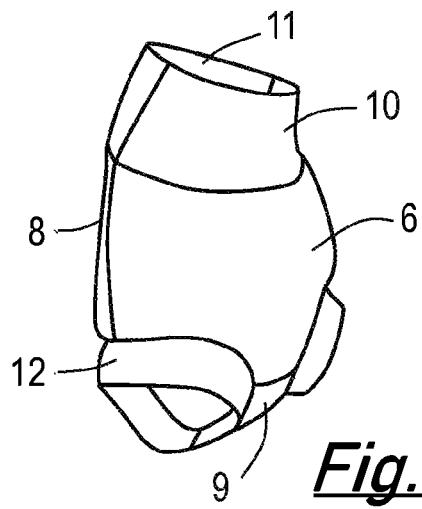
FIG. 6 is a perspective view, from the front, of the swim nappy of FIG. 3.
Figure 7:
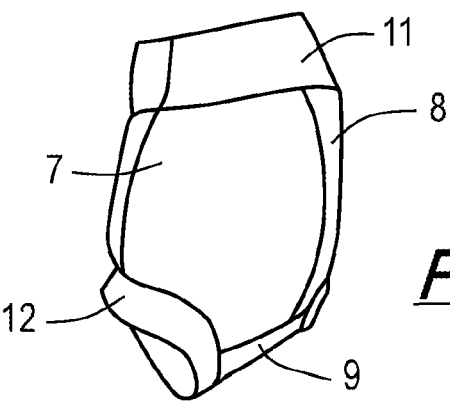
FIG. 7 is a perspective view, from the rear, of the swim nappy of FIG. 3.
Figures 8, 9:
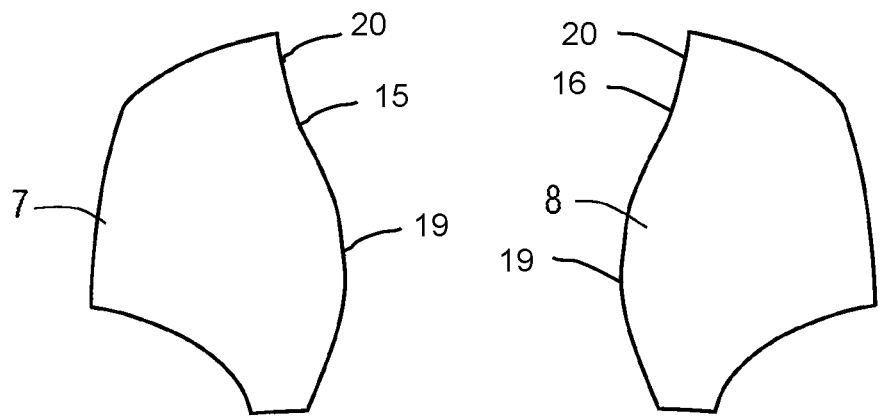
FIG. 8 is shows a rear panel of the swim nappy of FIG. 3.
FIG. 9 shows the other rear panel of the swim nappy of FIG. 3.
Figure 10:
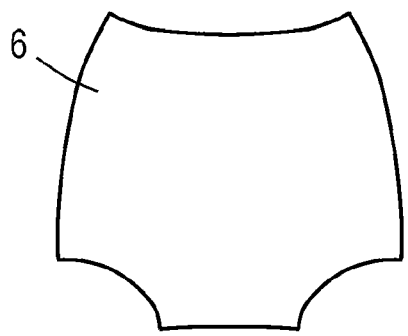
FIG. 10 shows the front panel of the swim nappy of FIG. 3.
Figure 11:
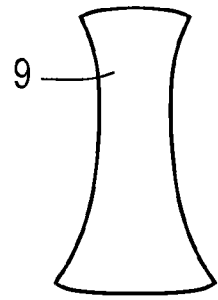
FIG. 11 shows the crotch panel of the swim nappy of FIG. 3.
Figure 12:
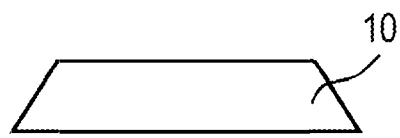
FIG. 12 shows the front panel of the waist band of the swim nappy of FIG. 3.
Figure 13:
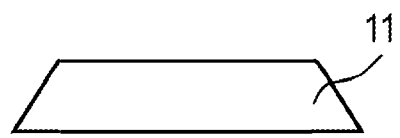
FIG. 13 shows the rear panel of the waist band of the swim nappy of FIG. 3.
Figure 14:
FIG. 14 shows a leg band of the swim nappy of FIG. 3.
Figure 15:
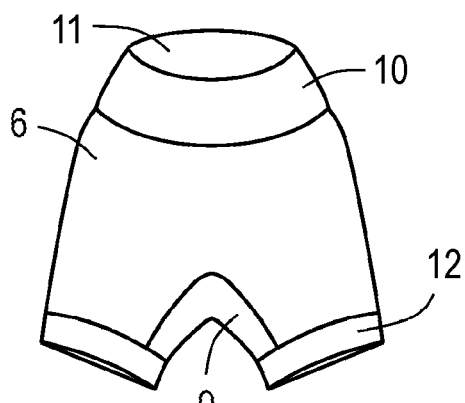
FIGS. 15-26 are corresponding views to FIGS. 3 to 14 of another embodiment of a swim nappy according to the invention.
Figure 16:
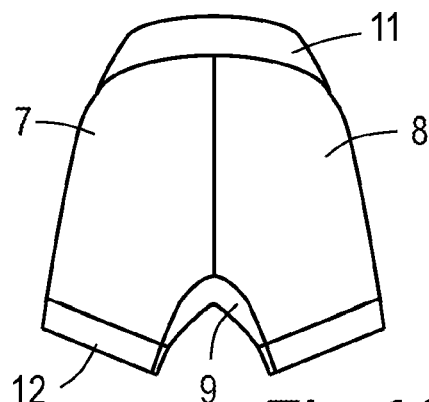
Figure 17:
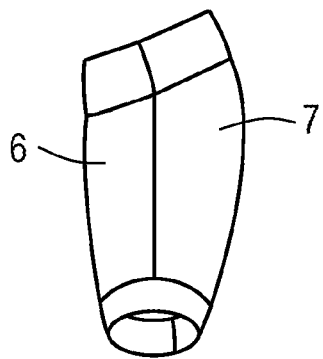
Figure 18:
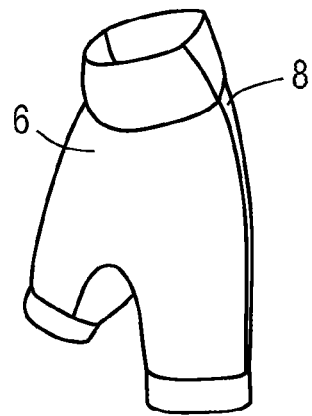
Figure 19:
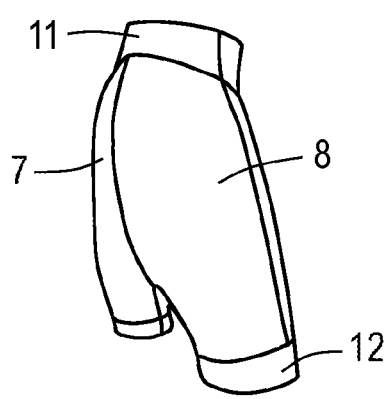
Figure 20:
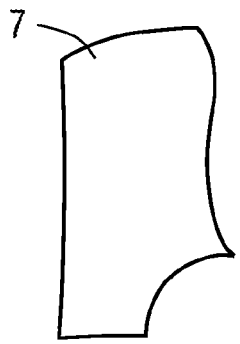
Figure 21:
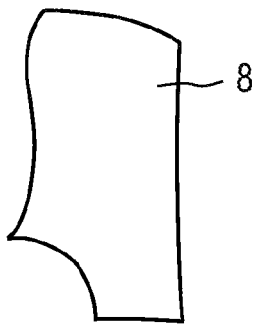
Figure 22:
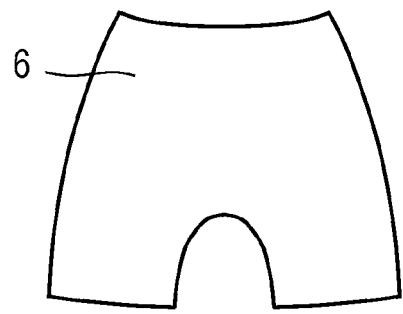
Figure 23:
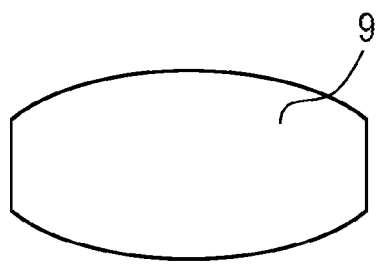
Figure 24:
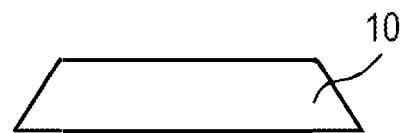
Figure 25:
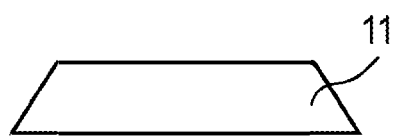
Figure 26:
Figure 27:
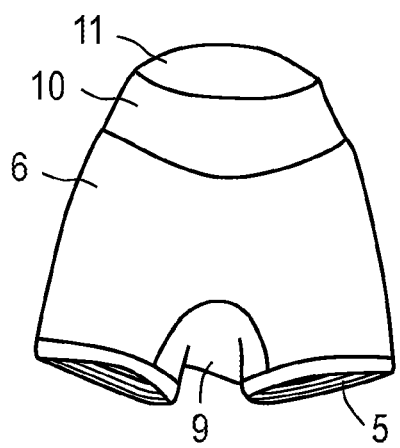
FIGS. 27-31 are corresponding views to FIGS. 3 to 7 of yet another embodiment of a swim nappy according to the invention.
Figure 28:
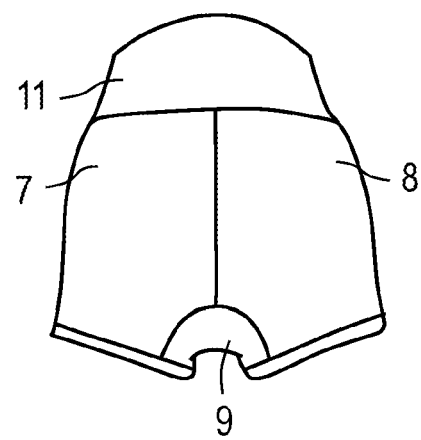
Figure 29:
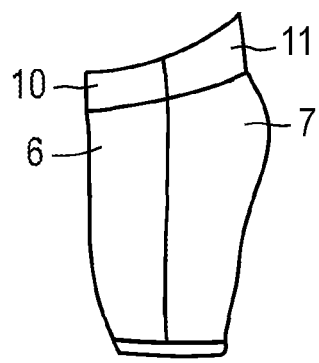
Figure 30:
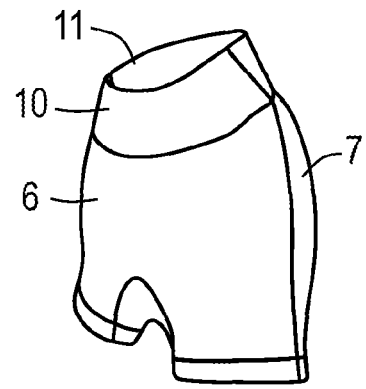
Figure 31:
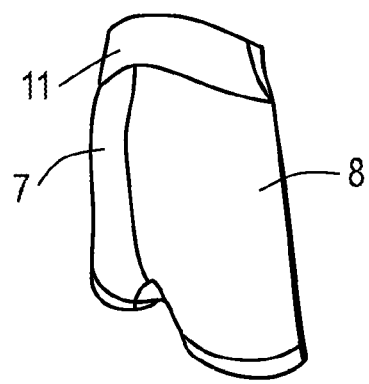

Referring first to FIGS. 1 and 2 there is shown one type of conventional swim nappy. It takes the form of a brief having substantially identical front and rear panels 1 of an impermeable material. These panels are stitched together along their side and bottom edges 2 along internal seams to form waist and leg openings. Elasticated waist and leg bands 3 are stitched around the waist and leg openings. The bands 3 are intended to form a seal around a wearer's waist and legs, thereby to keep any faecal matter discharged by the wearer in the garment. In practice, though, matter can leak from the garment via the waist and leg openings. One reason for this is that the waist and leg bands tend to come away from the wearer when the wearer moves. Since the garment is intended to be used when the wearer is active this is a problem.

Garments according to embodiments of the invention will now be described. The garments are intended to be worn whilst swimming by babies and very young children. They may be worn on their own, or over a suitable nappy liner. The garments could also be used by older children and adults suffering from bowel incontinence.

A first embodiment is illustrated in FIGS. 3 to 11. FIGS. 3 to 7 show the garment and FIGS. 8 to 14 show the outline shape of the panels forming the garment.

Referring to these drawings, the garment is a swim nappy and takes the general form of a brief.

The main body of the brief is formed from a single front panel 6, two rear panels 7 and 8, a crotch panel 9. These panels are all substantially impermeable and formed from an approximately 1 mm thick layer of neoprene laminated between two layers of synthetic woven fabric such as a polyester or nylon fabric. Owing to inclusion of the layer of neoprene the fabric is resiliently stretchable. The panels are further described below and are joined together to form a brief having waist and leg openings, the leg openings each extending at about a 45 degree angle to the waist opening.

Resiliently stretchable waist 10, 11 and leg 12 bands extend around each opening. The waist and leg bands are formed from a resiliently stretchable knitted fabric comprising a proportion of elastic fibre. In the described example the fabric is a tricot knit fabric formed from approximately 70% nylon and 30% elastane (spandex) fibres. This fabric has a greater degree of elasticity than the fabric forming the panels of the main body of the brief.

The front panel 6 has top, bottom and two side edges on opposite sides of the panel. It is symmetric about a vertical centre line extending between the top and bottom edges. The top edge is concave 17 and more steeply curved than that of the existing garment shown in FIG. 1. The opposed side edges are generally convex, and taper towards each other towards the top edge. The side edges meet the top edge at an approximate right angle. The bottom edge is formed from two concave curves extending respectively at an approximate right angle from the bottom of each side edge and each meeting a central substantially straight section at an approximate right angle.

The two rear panels 7, 8 each have top and bottom edges and opposed outer and inner side edges which are are mirror opposites of each other. The top and outer edges are convex. The outer edge is substantially the same length as the outer edges of the front panel 6. The top edge meets the outer edge at an obtuse angle. The opposite end of the top edge meets the inner edge at an approximate right angle. The inner edge is slightly concave adjacent the top edge and transitions into a convex shape, such that over its length the inner edge has the general shape of a full wave. The inner edge is longer than the outer edge. The bottom edge has a substantially straight portion which meets the inner edge at an obtuse angle, and a concave portion which extends from the opposite end of the straight portion to the lower end of the outer edge. The concave portion meets both the straight portion and the outside edge at obtuse angles. The height of the panel from the bottom edge to the top edge increases from the outer edge to the inner edge of the panel.

The crotch panel 9 has convex front and rear edges joined by concave sides and is symmetric about a centre line running between the front and rear edges. The front edge is the same length as the central substantially straight portion of the lower edge of the front panel 6, and the length of the rear edge is double that of the substantially straight portion of the lower edge of one rear panel 7, 8.

The waist band is formed from substantially identical front 10 and rear 11 panels, each being substantially trapezoidal in shape, having a substantially parallel upper edge 13 and lower edge 14, with the upper edge shorter than the lower edge. The height of each panel between its parallel sides is the same, about 6 cm in the current example.

The leg bands 10 are each formed from a single, elongate, generally rectangular panel of fabric, with a width of about 4 cm in the current example.

To form the garment the inner edges of the rear panels 7, 8 are stitched together with their respective ends aligned, the outer edge of each rear panel is stitched to a respective side of the front panel 6, again with their ends aligned. The front edge of the crotch panel 9 is stitched to the central substantially straight portion of the lower edge of the front panel 6 and the rear edge is stitched to the adjacent straight portions of the lower edge of the rear panels 7, 8. The panels are all stitched together with flat lock stitching, so that the edges of adjacent, joined panels abut each other. This forms the main body of the garment.

The lower edge of the front panel 10 of the waist band is stitched to the top edge of the front panel 6 with the respective ends of the edges aligned. Similarly, the lower edge of the rear panel of the waist band is stitched to the combined top edges of the two rear panels 7, 8. The panels 10, 11 of the waist band are stitched to front 6 and rear 7, 8 panels of the garment by way of internal seams. Respective sides of each panel 10, 11 of the waist band are stitched together with flat lock stitching to form a continuous loop. As the panels 10, 11 making up the waist band are trapezoidal the length of the top, free edge of the waist band is longer than the bottom edge, which is fastened to the main body of the garment. The height of the panels 10, 11 forming the waist band, from their bottom edge to top edge, is a minimum of about 25% of the overall height of the garment from the top edge of the waist band to the underside of the crotch panel.

A long edge of each leg band 10 panel is stitched around each leg opening formed by an outer concave portion of the lower edge of the front panel 6, the concave portion of the lower edge of the adjacent rear panel 7, 8 and the adjacent side of the crotch panel 9. The long edge of the leg band 10 panel is the same length as the combined length of the edges of other panels to which it is stitched so the leg band completely encircles the leg opening. Opposite short ends of the leg band panel are then stitched together to form a continuous band.

A second embodiment is illustrated in FIGS. 15 to 26. FIGS. 15 to 19 show the garment and FIGS. 20 to 26 show the outline shape of the panels forming the garment. The same reference numerals are used in the drawings to identify corresponding features to those shown in FIGS. 3 to 14.

Referring to these drawings, the garment is a swim nappy and takes the general form of a pair of shorts or trunks.

The shorts are formed from a single front panel 6, two rear panels 7, 8 and a crotch panel 9. These panels are formed of the same material as the corresponding panels of the first embodiment and are joined together to form a brief having waist and leg openings, the leg openings each extending generally parallel to the waist opening.

Resiliently stretchable waist 10, 11 and leg 12 bands extend around each opening, formed form the same material as those of the first embodiment.

The front panel 6 has top, bottom and two side edges on opposite sides of the panel. It is symmetric about a vertical centre line extending between the top and bottom edges. The top edge is concave. The opposed side edges are convex and taper towards each other towards the top edge. The side edges meet the top edge at an approximate right angle. The bottom edge is formed from two substantially straight, aligned sections each extending at an approximate right angle from a respective bottom of each side edge towards each other and to a respective opposite side of a central U-shaped section which serves to define two legs to the garment.

The two rear panels 7, 8 each have top and bottom edges and opposed outer and inner side edges which are are mirror opposites of each other. The top and outer edges are convex 18. The outer edge is substantially the same length as the outer edges of the front panel 6. The top edge meets the outer edge at an obtuse angle. The opposite end of the top edge meets the inner edge at an approximate right angle. The inner edge is slightly concave 20 adjacent the top edge and transitions into a convex shape 19, such that over its length the inner edge has the general shape of a full wave. The inner edge is longer than the outer edge. The bottom edge has a substantially straight portion which meets the inner edge at an obtuse angle, and a concave portion which extends from the opposite end of the straight portion to the lower end of the outer edge. The concave portion meets both the straight portion and the outside edge at obtuse angles. The height of the panel from the bottom edge to the top edge increases from the outer edge to the inner edge of the panel.

The crotch panel 9 has substantially straight front and rear edges joined by convex sides and is symmetric about a centre line running between the front and rear edges. The front edge is the same length as the central U-shaped portion of the lower edge of the front panel 6, and the length of the rear edge is double that of the concave portion of the lower edge of one rear panel 7, 8.

The waist band is formed from front 10 and rear 11 panels which are of approximately the same shape as those of the first embodiment.

As with the first embodiment, the leg bands 10 are each formed from a single, elongate, generally rectangular panel of fabric.

The main body of the garment is formed by joining the front, rear and crotch panels as with the first embodiment, the only differences being that the front edge of the crotch panel 9 is stitched to the central U-shaped portion of the lower edge of the front panel 6 and the rear edge is stitched to the adjacent concave portions of the lower edge of the rear panels 7, 8. The rear panels 7, 8 are joined together along adjacent curved edges 15, 16.

The panels forming the waist band are joined to the front and rear panels as with the first embodiment. The height of the panels 10, 11 is about a minimum of about 25% of the overall height of the garment from the top edge of the waist band to the underside of the top of the crotch panel, when in use, worn by a wearer.

As with the first embodiment, a long edge of each leg band 10 panel is stitched around each leg opening, in this case formed by the straight portions of the lower edge of the front 6 and rear 7, 8 panels. The long edge of the leg band 10 panel is the same length as the combined length of the edges of other panels to which it is stitched so the leg band completely encircles the leg opening. Opposite short ends of the leg band panel are then stitched together to form a continuous band.

A third embodiment is illustrated in FIGS. 27 to 31. The same reference numerals are used in the drawings to identify corresponding features to those shown in FIGS. 15 to 19.

This garment is the same as that shown in FIGS. 15 to 27 except that the leg bands 12 are omitted. Instead a band of silicone rubber 5 extends around the inside of each leg opening which, in use, helps form a seal with a wearer's leg. The inherent elasticity of the fabric of the front 6 and rear 7, 8 panels forming the legs of the garment is sufficient to keep the seal in contact with the wearer's leg. The rubber enables a satisfactory seal to be achieved without the need for an elasticated leg band and so enables the design of the garment to be changed, omitting the elasticated leg bands, without compromising its functionality.

The shapes of the various panels making up all of the described garments contribute to producing garments with an improved fit compared to existing swim nappies, and particularly an improved fit which reduces the risk of the waist and leg bands or seals coming away from a wearer's body when in use, allowing material contained within the garment to escape.

The shape of the front 6 and rear 7, 8 panels is such that, in use, the top edge of the front panel sits lower on the wearer's body than the top edges of the back panels. The shape of the panels 10, 11 of the waist band builds on this feature with the top edge of the front of the waist band sitting lower on the wearer's body than top edge of the back of the waist band.

A lower top edge to the front of the garment positions the edge to the bottom of, or below, the wearer's stomach and therefore below a natural point of bend. This, coupled with the use of an elastically stretchable fabric for the panels of the waist band reduces the risk of the front of the waist band rolling down the wearer in use, and causing a leak of material from the garment.

A higher top edge to the back of the garment positions the edge part way up the wearer's back, above the wearer's coccyx and/or largest spinal cavity. This reduces the risk of the back of the waist band coming away from the wearer owing to the concavity towards the base of their spine.

As the top edge of the waist band is shorter than its bottom edge, the waist band closely fits the form of the wearer's body extending up from the top of the main body of the garment.

The opposed, mirrored, curved inner edges of the rear panels 7, 8 of the garment cause the panels to adopt a curved shape which fits over a wearer's buttocks when the panels are stitched together. Provision of a separately formed crotch panel further contributes to an improved fit, and to forming a garment which defines a volume shaped to accommodate a wearer, in contrast to the generally flat conventional garment shown in FIGS. 1 and 2. These features both improve the fit of the garment to a wearer's body. As the garment better fits the shape of a wearer's body it is less reliant on its inherent elasticity to accommodate the wearer's form. This reduces the amount of strain on the garment, particularly when the wearer moves. This in turn reduces the risk of the leg or waist bands or seals being pulled out of contact with the wearer's body and so minimises any escape of material contained in the garment.

The above embodiments are described by way of example only. Many variations are possible without departing from the scope of the invention.

The invention claimed is:

1. A swim diaper for an infant or baby formed from panels and configured to cover a wearer's body between the waist and thighs, the swim diaper comprising:
    a waist band and a remainder of the swim diaper,
    the waist band formed from one or more panels of material, the waist band formed from a resiliently stretchable fabric which is tricot knitted, the waist band having a top edge and bottom edge, the top edge being shorter than the bottom edge and the bottom edge being joined to a top edge of the remainder of the swim diaper, and
    the remainder of the swim diaper comprising two rear panels joined together along adjacent curved edges,
    wherein a rear of a top edge of the remainder of the swim diaper is convex relative to a rear of the remainder of the swim diaper and a front of the top edge of the remainder of the swim diaper is concave relative to a front of the remainder of the swim diaper such that the swim diaper is shaped so that, in use, the top edge of the waist band at a rear of the swim diaper extends beyond the top edge of the waist band at a front of the swim diaper so that the swim diaper is configured to extend further up the wearer's back than the wearer's front when the wearer is standing upright.

2. A swim diaper as claimed in claim 1 configured so that a top edge of the rear of the swim diaper extends above the wearer's coccyx, in use.

3. A swim diaper as claimed in claim 1 wherein the waist band is formed from one or more panels of fabric which are substantially trapezoidal in shape and a shorter parallel side or sides of the or each panel form the top edge of the waist band.

4. A swim diaper as claimed in claim 1 wherein the two rear panels are mirror opposite rear panels and are joined together along adjacent opposed curved edges.

5. A swim diaper as claimed in claim 4 wherein the opposed curved edges have both concave and convex portions.

6. A swim diaper as claimed in claim 1 wherein the remainder of the swim diaper comprises a front panel having opposite side edges each joined to a respective side edge of a rear panel.

7. A swim diaper as claimed in claim 1 wherein the remainder of the swim diaper comprises a crotch panel configured to extend between a wearer's legs in use.

8. A swim diaper as claimed in claim 7, wherein the remainder of the swim diaper comprises a front panel having opposite side edges each joined to a respective side edge of a rear panel, and wherein the crotch panel is joined to a lower edge of each rear panel, and a lower edge of the front panel.

9. A swim diaper as claimed in claim 8 wherein the waist band extends above the top edge of the swim diaper by a distance which is at least 20% of the shortest distance between a point on a lower edge of the front or rear panel to which the crotch panel is joined and a top edge of the front or rear panel at which the waist band is joined.

10. A swim diaper as claimed in claim 1 wherein the remainder of the swim diaper comprises leg bands.

11. A swim diaper as claimed in claim 10 wherein the leg bands are resiliently stretchable.

12. A swim diaper as claimed in claim 1 wherein the remainder of the swim diaper comprises a seal which is disposed around an inside of each leg opening and/or waist opening and configured to form a seal with a wearer's body, in use.

13. A swim diaper as claimed in claim 1 having the form of a brief or a pair of shorts or trunks.

14. A method of reducing contamination of a swimming pool by an individual comprising the steps of:
 providing a swim diaper according to claim 1; and
 wearing of the swim diaper, by the individual, whilst in the swimming pool.

\* \* \* \* \*